United States Patent [19]

Faierstain

[11] Patent Number: 5,716,209
[45] Date of Patent: Feb. 10, 1998

[54] PLASTERLESS MOUNTING DENTAL ARTICULATOR

[76] Inventor: Paul B. Faierstain, 20090 Rodriquez Ave., Cupertino, Calif. 95014

[21] Appl. No.: 510,450

[22] Filed: Aug. 2, 1995

[51] Int. Cl.⁶ ............................................. A61C 11/08
[52] U.S. Cl. ............................................. 433/60
[58] Field of Search ..................... 433/60, 74, 213, 433/63, 65, 61

[56] References Cited

U.S. PATENT DOCUMENTS

| | | |
|---|---|---|
| 565,326 | 8/1896 | Bragg et al. |
| 2,621,407 | 12/1952 | Schlesinger ............... 433/60 |
| 2,731,723 | 1/1956 | Brandhandler ............ 433/60 |
| 2,911,722 | 11/1959 | Benfield et al. ........... 433/60 |
| 3,808,689 | 5/1974 | Spinella .................... 433/60 |
| 4,169,314 | 10/1979 | Mercer et al. ............. 433/60 |
| 4,200,981 | 5/1980 | Fine .......................... 433/60 |
| 4,337,039 | 6/1982 | Martin et al. .............. 433/60 |
| 4,338,884 | 7/1982 | Atchley et al. ............ 119/72.5 |
| 4,358,269 | 11/1982 | Hay et al. .................. 433/60 |
| 4,371,338 | 2/1983 | Mercer et al. ............. 433/60 |
| 4,382,787 | 5/1983 | Huffman .................... 433/64 |
| 4,460,338 | 7/1984 | Mercer et al. ............. 433/60 |
| 4,494,934 | 1/1985 | Huffman .................... 433/213 |
| 4,496,320 | 1/1985 | Hwang et al. .............. 433/60 |
| 4,744,751 | 5/1988 | Finkelstein et al. ....... 433/60 |
| 4,854,868 | 8/1989 | Pitre ........................... 433/60 |
| 5,352,117 | 10/1994 | Silva ........................... 433/60 |

FOREIGN PATENT DOCUMENTS 911054  6/1946  France .................. 433/60

OTHER PUBLICATIONS

Small Parts, Inc. Catalog No. 14 1994, Rod Ends Without Studs, Part No. A-REJF-4, thread size ¼-28, p. 269 (2 sided page).

Zahn Dental Company, Inc., Zahn Dental Catalog 1995-1996, The Reference Book, pp. 46-48 (1995).

*Primary Examiner*—Cary E. O'Connor
*Attorney, Agent, or Firm*—Skjerven Morrill Macpherson Franklin and Friel; Thomas S. MacDonald

[57] ABSTRACT

A dental articulator has a generally flat fixed base and a pivoted top with trays mounted on both the base and top. The trays have upstanding side wall elements, each tray being dimensioned and spaced for reception of a hard mold member having a generally flat top surface mounting a positive cast or dental model of one of a patient's arches. The peripheral edge portions of the hard mold members are dimensioned to be press fitted into the trays to abut juxtaposed ones of side wall elements of the tray. The trays are each slidable in Y or X-y axes with respect to substages connected to the articulator top and articulator base, respectively. Each tray has a straight rear wall, with the remainder of a continuous wall being in straight or curved interior segments. In one embodiment, a series of posts define the internal periphery of the trays.

20 Claims, 5 Drawing Sheets

PLASTERLESS MOUNTING DENTAL ARTICULATOR

The present invention relates to dental models and more particularly to a novel dental articulator and tray for mounting the dental mode.

BACKGROUND OF THE INVENTION

A dental articulator is used for mounting dental models to make it possible to reproduce the movement and relative position of the jaws of a patient on whose jaws dentures or crowns are to be fitted. In order to construct an acceptable denture or crown the dentist makes a negative impression of the affected tooth or teeth. The negative impression of the patient's arches is then processed normally in a dental laboratory to become a mold into which a material for forming positive dental casts is poured. These positive casts are duplicates of the patient's arches with or without teeth and will then become the primary model to which the denture or crown is to be constructed. The dental casts are then mounted in an articulator to permit arrangement of the dentures or crowns in their proper position for occlusion.

Articulators have been used in the making of dentures for at least a century as evidenced by U.S. Pat. No. 565,326 issued Aug. 4, 1896. Such articulator and most all articulators have employed a hinged and lateral and angular and adjusting mechanism for aligning an upper jaw model and a lower jaw model. Most of the dental models are held by plaster in a top and bottom half of the articulator. U.S. Pat. No. 3,808,689 which also shows a dovetail key and keyway for a tray engagement is typical. U.S. Pat. No. 4,337,039 and U.S. Pat. No. 4,358,269 showed prior plasterless mounting dental articulators, the first involving a ferromagnetic disc in the base of a dental model, the second employing countersunk cutter stops which engage cavities in the perimeter a matched set of casts. U.S. Pat. No. 4,371,338 and U.S. Pat. No. 4,460,338 show articulators which have thumb-screw pins for holding and adjusting the dental cast. In the latter patent, a special curved articulator top is needed. In U.S. Pat. No. 4,382,787 the casts are mounted on arms of the articulator which extend into slots of the cast, with spherical ball joints provided between the arms and a hinged element. U.S. Pat. No. 4,200,981 describes a dental articular and tray system where the dental model is adhesively secured to the tray. U.S. Pat. No. 4,494,934 illustrates a dental model base per se for use in an articulator. U.S. Pat. No. 5,352,117 shows a dental replica which is snap-fitted using internal bores in the replica and upstanding snap posts on plates bonded to articulator frame members.

SUMMARY OF THE INVENTION

The invention utilizes a hard mold member which after separating the dental model from a flexible, soft mold and mounting the dental model on the hard mold member, the hard mold member is placed in a tray that is part of the articulator. The hard mold member has an outer periphery which has substantially the same dimension and general shape as the inner periphery of a lip surrounding the tray top. The lip has the ability to hold the hard mold member periphery in abutment position to at least portions of the lips. The hard mold member is designed to fit substantial all models used for making dentures or crowns, either of small, medium or large size, and including left or right quadrants of a mounted dental model.

In one embodiment each tray has an internal periphery which conforms to the peripheral shape of the hard mold members such that the hard mold member is easily press-fitted therein. In another embodiment the inner periphery of the tray is a series of straight walls, including a rear straight wall on which abuts a rear straight wall of the hard mold member received in the tray. A normally curved remaining peripheral wall of the hard mold number provides a series of abutting tangential line contacts with the other straight walls. In a third alternative the tangential point contacts can be provided by a series of posts upstanding from a flat tray bottom which are spaced the same as the tangential line contacts in the second embodiment. Further, the invention contemplates that the trays are slidably mounted with respect an articulator base and a pivoted top thereof. This is accomplished either by a tongue and groove dovetail slide or by a slotted articulator base and a slotted articulator top each clamped to respective trays. In a preferred embodiment, a lateral slide is integrated with the longitudinal slide so that the bottom tray on the articulator base can be moved in both X (lateral) and Y (longitudinal) orthogonal axes.

The present invention is a further simplification of the mechanical mounting of dental casts models. Almost all of the dental articulators built to date have been built for use with plaster or adhesive mounting techniques. Other mounting devices have been built using a claw type of clamping device in an attempt to find a technique other than the use of plaster or adhesive. These alternative mounting techniques have been far less than satisfactory especially when the dental model (sometimes called dental casts) are to be removed and remounted to their original positions in the articulator for rework of the crown or denture. This is an absolute requirement except for the most simple crown and bridge work. The invention solves the above problems by locating the hard mold member at fixed positions or at line contacts in metal trays slidably mounted on each of the articular base and the articulator pivoted top. The holding means of the articulator does not disturb these fixed positions and dental casts are easily removed and remounted in their original positions.

The invention provides an articulator in which the teeth casts or models can be mounted without the use of plaster or adhesive thus making the possibility of transfer from one case i.e. the upper and lower models of one patient, to those of another patient. The invention may also be used to modify the current state of the art articulators by converting them through the use of a retrofit or conversion kit, from a plastermount articulator to a plasterless articulator. The articulators so adapted can be used for the rapid removal of and remounting of the casts to their originally adjusted position in the articulator where it is necessary to further process the tooth or bridge being constructed by the technician using the articulator-mounted casts. When the dental models are secured in position in the trays there is minimal risk of damaging the models. The models on their hard mold member may be released as desired and remounted in the original precise position at any given time without major adjustment, with faster and more accurate processing. In another aspect of the invention a long threaded chamber leading to the ball bearing articulating top joint is provided to allow a high degree of pressure to be put on the standard rod end ball bearing of the pivoting top without a problem of stripping the thread.

The articulator has a generally flat fixed base and a pivoted top with a first tray mounted on the base. The tray includes upstanding first side wall elements dimensioned and spaced for reception of a hard mold member having a generally flat surface mounting a positive cast of one of a patient's arches. At least multiple peripheral edge portions of the hard mold member are dimensioned to abut juxtaposed ones of the side wall elements. A second tray depends from the articulator pivoted top and faces the first tray. The second tray also includes second side wall elements dimensioned and spaced for reception of a second hard mold member having a generally flat surface mounting a positive cast of a second of a patient's arches. At least multiple peripheral edge portions of the second hard mold member are dimensioned to abut juxtaposed ones of the second side wall elements.

DETAILED DESCRIPTION

A dental base is formed by pouring yellow stone into a mold (not shown). The mold standardizes the width, height and configuration of the molded base. The yellow stone will flow beneath and around a mold shelf and up to a level coincident with the top of a continuous sidewall of the model. A screed or the like may be employed to obtain a level top surface of the yellow stone. Before the yellow stone sets, a tooth die (pink stone) having a plurality of dowels or pins depending therefrom is placed upon the uncured exposed surface of base. Preferably, the protruding pair of pins is commensurate in length with the thickness of the interior yellow stone mold. The pins are coated with a release agent to permit sliding disengagement from the soft mold after the yellow stone is cured. The dental model is then removed from the soft mold. The mold is rubber-based and the dental model is mounted by pins onto the resultant hard mold member, typically of yellow stone, premounted in the articulator. The individual teeth which are to be worked on by the technician are sawed perpendicularly down so that they can be removed with a bottom pin as seen in U.S. Pat. No. 4,338,884. The hard mold members may also be made of polycarbonate with 30% glass fibers therein.

Figure 1:
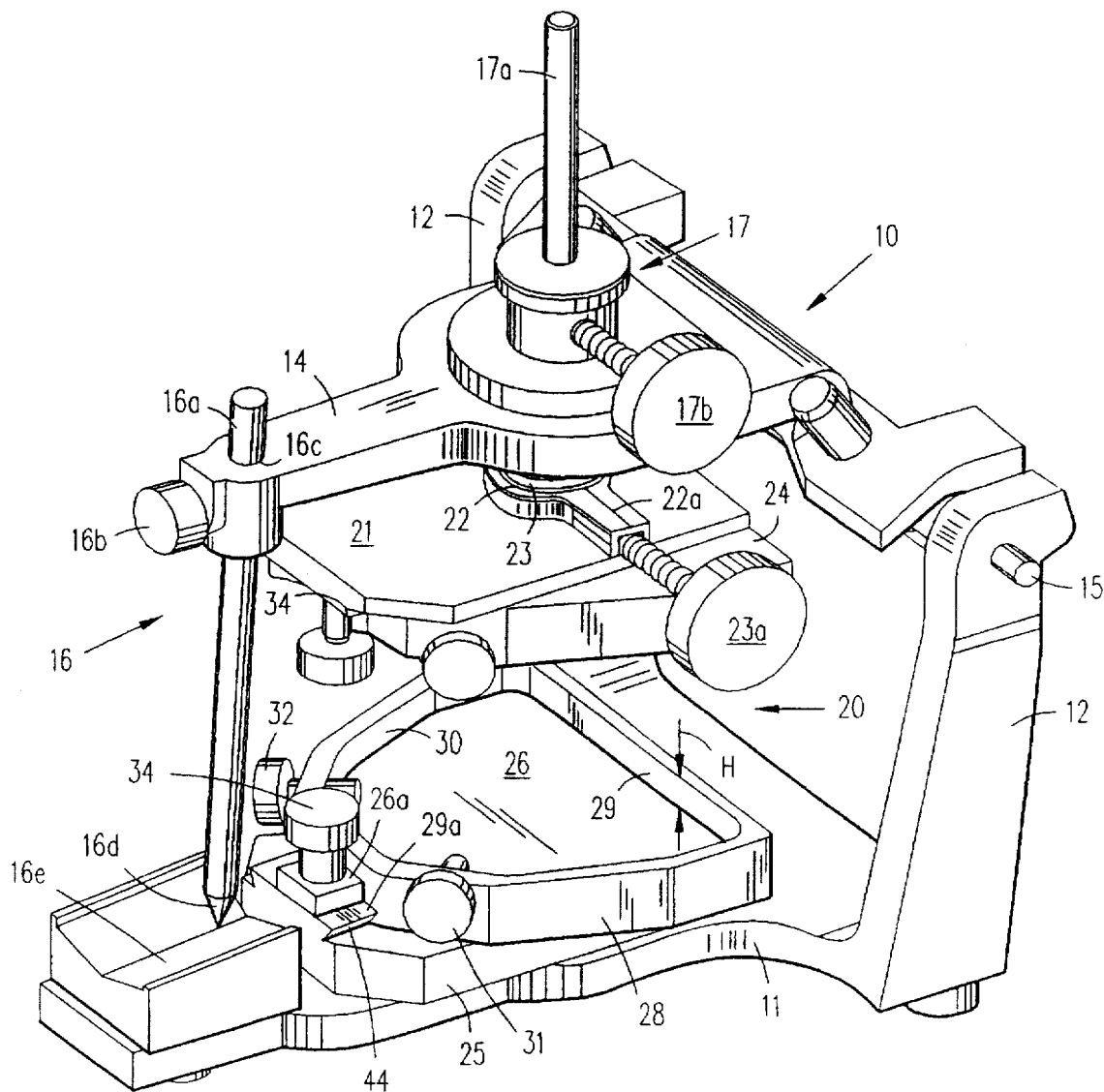
FIG. 1 is a perspective view of an articulator incorporating the conversion kit including trays of the invention.

FIG. 1 illustrates a typical articulator 10 which incorporates the present invention. The prior art articulator includes a substantially horizontal base 11, vertical support members 12, a top 14 pivoted to support members 12 about a pivot rod 15 or mounting balls (not shown); and a top height adjustment 16 comprising a rod 16a slidable in a top aperture 16c and held in a particular vertical position by thumb screw 16b. The distal end 16d of the rod in an articulator top "down" orientation abuts surface 16e on the articulator base to place the top 14 at a desired angle with respect to the supports 12. A top articulation setting adjustment 17 includes a rod 17a and thumb screw 17b, and a top subplate (not shown) which is mounted typically by a ball joint and positioned by setting thumb screw 17b for universally adjusting the angularity of the subplate. As discussed above in the Background of the Invention and as shown in Zahn Catalog 1995, page 47 in the illustrated NEY Dental Hoby L device, an articulator as described above has been heretofore used to mount a dental model by the use of plaster or adhesive between the subplate and the base.

Figure 7:
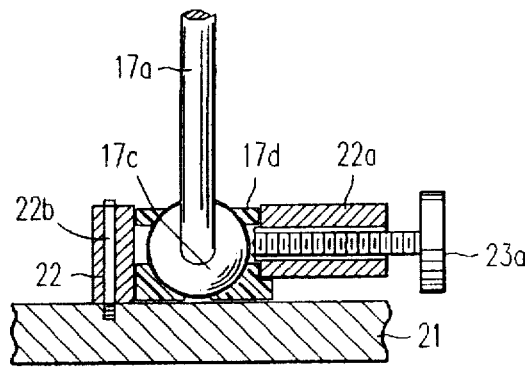
FIG. 7 is a sectional side view of the ball rod end joint within the upper substage.

In the present invention, a conversion or retrofit kit 20 is provided which fits internally of articulator 10. The conversion kit 20 includes a first subplate 21 including a slide (FIG. 2 or FIG. 10) on the underside of the subplate; a ring 22 connected to the subplate 21 by screws 22b (FIG. 7) and incorporating a ball rod end joint 23 therein; and a thumb screw 23a for fixing an angular position of the subplate. The rod end is a steel bar with an injection molded fiberglass reinforced nylon raceway 17d (FIG. 7) permanently reinforced with molybdenum disulfide with a hardened alloy steel ball providing free movement with minimum play. The rod end is available from Small Parts Inc. Catalog No. 14 1994, page 215 as No. KREJF-¼" (0.64 cm.) bore without stud. A long threaded chamber 22a leading to the ball joint 23 at the rod end ball bearing 17c and extending radially from ring 22 receives a threaded thumb screw 23a to allow a high degree of pressure to be put on the rod end ball bearing without stripping the threads. An inverted first tray 24 including an integral slide (FIG. 2) on a top surface, which slides with respect to the subplate slide permits linear longitudinal Y axis movement of the tray with respect to the subplate. Typically, the slides are dovetail slides formed by machining or otherwise, including a dovetail groove and dovetail tongue in the facing surfaces of the tray and subplate. The conversion kit 20 also includes a second subplate 25 attached to base 11 and having a similar or other longitudinal linear slide (FIG. 2) and, in a preferred embodiment (FIG. 10) also a lateral X axis slide, extending on a top surface of the second subplate. A second upright tray 26 with an integral slide on its bottom surface slides linearly longitudinally or also linearly laterally (FIG. 10) with respect to the second subplate slide. The inverted tray 24 and the upright tray 26 are duplicates of each other as are the longitudinal slide mechanisms.

Figure 3:
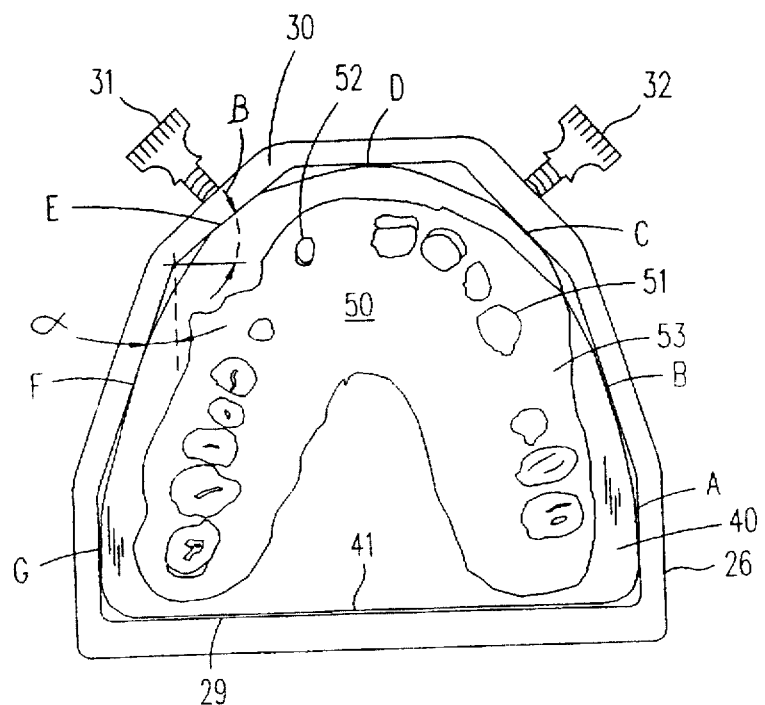
FIG. 3 is a plan view of one embodiment of a tray showing an inserted hard mold member with a mounted dental model.

The details of the trays will be described with respect to tray 26. Each of the trays is bounded by a peripheral lip or wall 28 surrounding the trays. Each wall includes a straight rear wall 29 and in one embodiment, a series of straight wall segments 30 completing a continuous wall from the ends of rear wall 29. The inner periphery of the wall is sized and shaped to approximate the outer peripheral contour of a hard mold member mounting the dental model. The wall height H is approximately ⅓ of the height of the hard mold member. In a standard size, the hard mold member has a height of about 15 mm and the internal wall has a height of about 5 mm. The normally curved remaining internal peripheral wall of the hard mold member provides a series of abutting tangential line contacts with a medial part of each wall segment 30, as seen in FIG. 3. A pair of thumb screws 31, 32 having non-piercing flat ends are positioned adjacent points C and E to abut on the hard mold member and to hold the straight back end 41 of the hard mold member against straight wall segment 29. A thumb screw 34 is provided to lock tray 26 with respect to subplate 25. Locking pin 34 is threaded through a threaded bore in an integral tray tab 26a extending laterally from the front of the tray (FIGS. 1 and 4).

Figure 2:
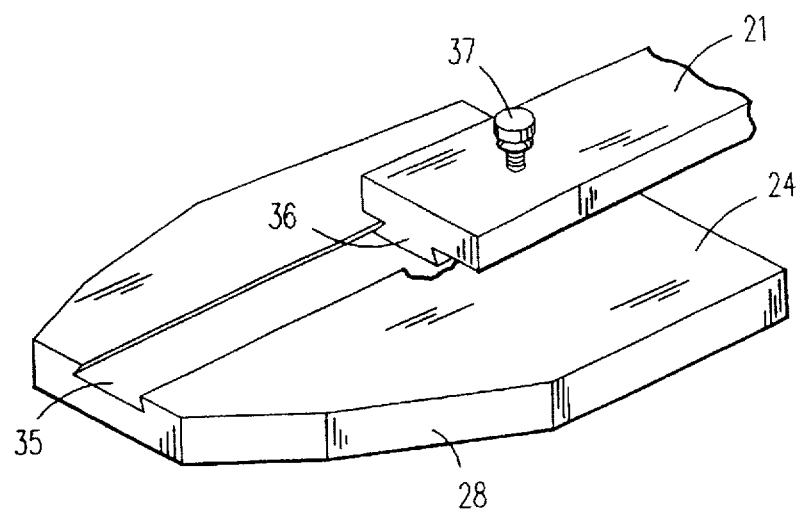
FIG. 2 is a perspective partial view of an articulator substage and tray sliding connection.

FIG. 2 illustrates the slides between a subplate 21 and an inverted tray 24 comprising a longitudinal dovetail groove or slot 35 in the underside of the tray 24 and a longitudinal dovetail tongue 36 extending from the underside of subplate 21. A clamping thumb screw 37 may extend through the subplate 21 and the tongue 36 and be screwed in to abut the bottom of groove 35 and lock the tray 24 with respect to the subplate 21. In this embodiment, no tab extends from the tray to support screw 37. The slide embodiment of FIG. 1 is preferred since access to pin 34 is from the top of the slide rather from underneath base 11.

FIG. 3 shows the mounting of a hard mold member 40 and an included dental model 50 in the tray. The hard mold member 50, again normally made of yellow stone mounts a dental model 50 again normally made of pink stone, which on a top surface has normal tooth protrusions 51 and tooth posts 52 (representing teeth ground down by a dentist) for bridge connections and spaces 53 representing missing teeth or gaps between teeth, in the form of a patient's tooth arch. The hard mold member 50 has a straight section 41 which abuts the straight wall 29 of the tray while curved parts of the hard mold member makes tangential line contacts at points A, B, C, D, E, F and G on the straight wall sections of the tray. The angular wall sections typically have angles α and β of 20° and 45° respectively. The hard mold member is in a snap press fit in the tray. The term "snap press" as used herein means that the hard mold member may be easily pushed into the tray interior with a minimum of clearance (about 10–20 microns) between the hard mold member periphery and the inner periphery of the tray with the thumb screws retracted. In order to hold the hard mold member at a fixed locating surface thumb screws 31, 32 are threaded inwardly to abut the member so that hard mold member is prevented from inadvertently dropping out of the trays. Thus, each time that a dental model (and its attached hard mold member) is inserted into the tray, the dental model is at the same spacial position in the tray. If desired, numbered line indicia 44, e.g. 0–50 mm, may be placed on the slides to indicate a desired longitudinal or lateral position of the tray with respect to the subplate. A transverse straight edge 29a (FIG. 1) parallel to the straight edge 29 of the tray may be lined up with a desired indicia line to indicate a desired position of the tray relative to the subplate. In a further modification, the hard mold member may have an outer peripheral shape which conforms to and closely fits within the straight walls of the interior of the trays.

Figure 4:
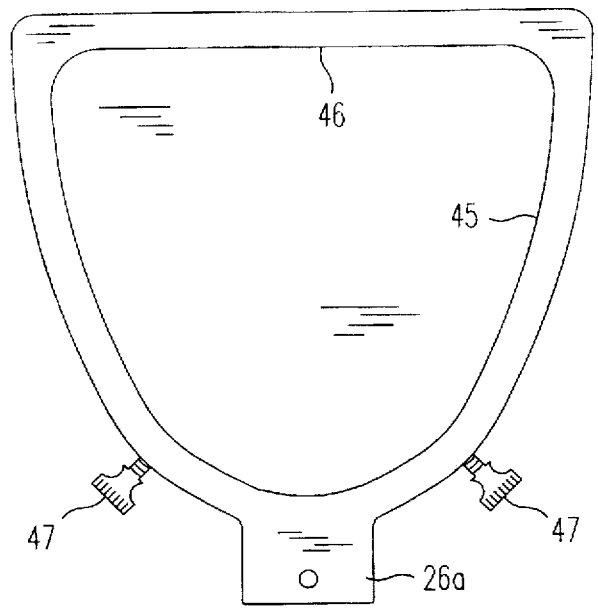
FIG. 4 is a plan view of a second embodiment of the tray with an inserted hard mold member (without a dental model).

In a second embodiment as seen in FIG. 4, the tray may have a lip or wall 45 which is internally curved on all but a straight section 46, to conform to the outer curvature of the hard mold member 40. The hard mold members are snap press-fitted into each tray and thumb screws 47 are turned to hold the hard mold member in the tray, against most of the tray walls, particularly flush against straight wall 46.

Figure 5:
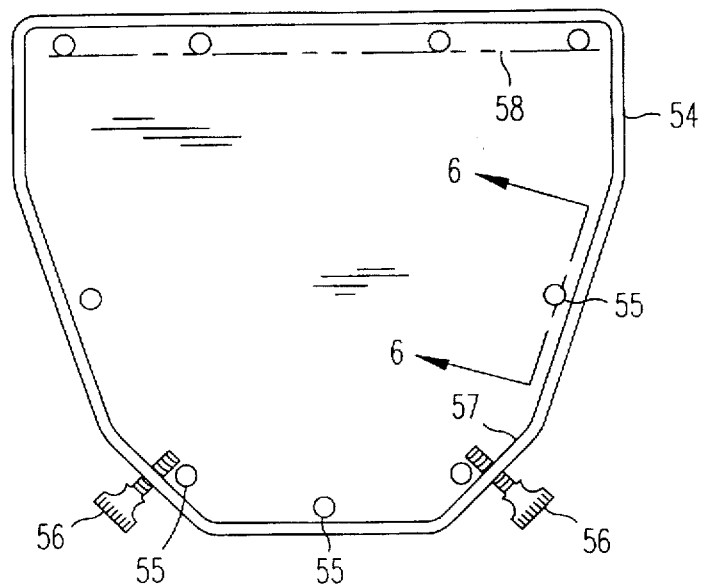
FIG. 5 is a plan view of a third embodiment of a tray per se.
Figure 6:
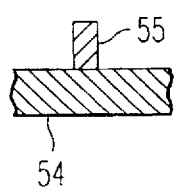
FIG. 6 is a section view taken on the line 6—6 of FIG. 5 showing the post thereof.

In a third embodiment as seen in FIGS. 5 and 6, a series of spaced upstanding posts 55 (depending posts in the top inverted tray) are provided at locations on the tray base 54 corresponding at least to points A, B and F, G of FIG. 3. posts may also be provided at points C and D or at intermediate locations between any two adjacent points A–B, B–C etc. (as seen in FIG. 3) which are all spaced to allow a hard mold member to be snap press-fitted within the confines of all the posts and in tangential line contact with the posts. As in FIG. 3, the post height preferably will be the same, i.e. 5 mm, as the height of the interior periphery of the tray wall. Each of a pair of thumb screws 56 are screwed into an integral side bracket 57 and can be screwed in to hold the hard mold member in the tray and against an inner tangent line 58 of the posts 55 extending along a straight end section of the tray, which corresponds to the straight section 41 of the hard mold member (not shown in FIG. 5).

Figure 8:
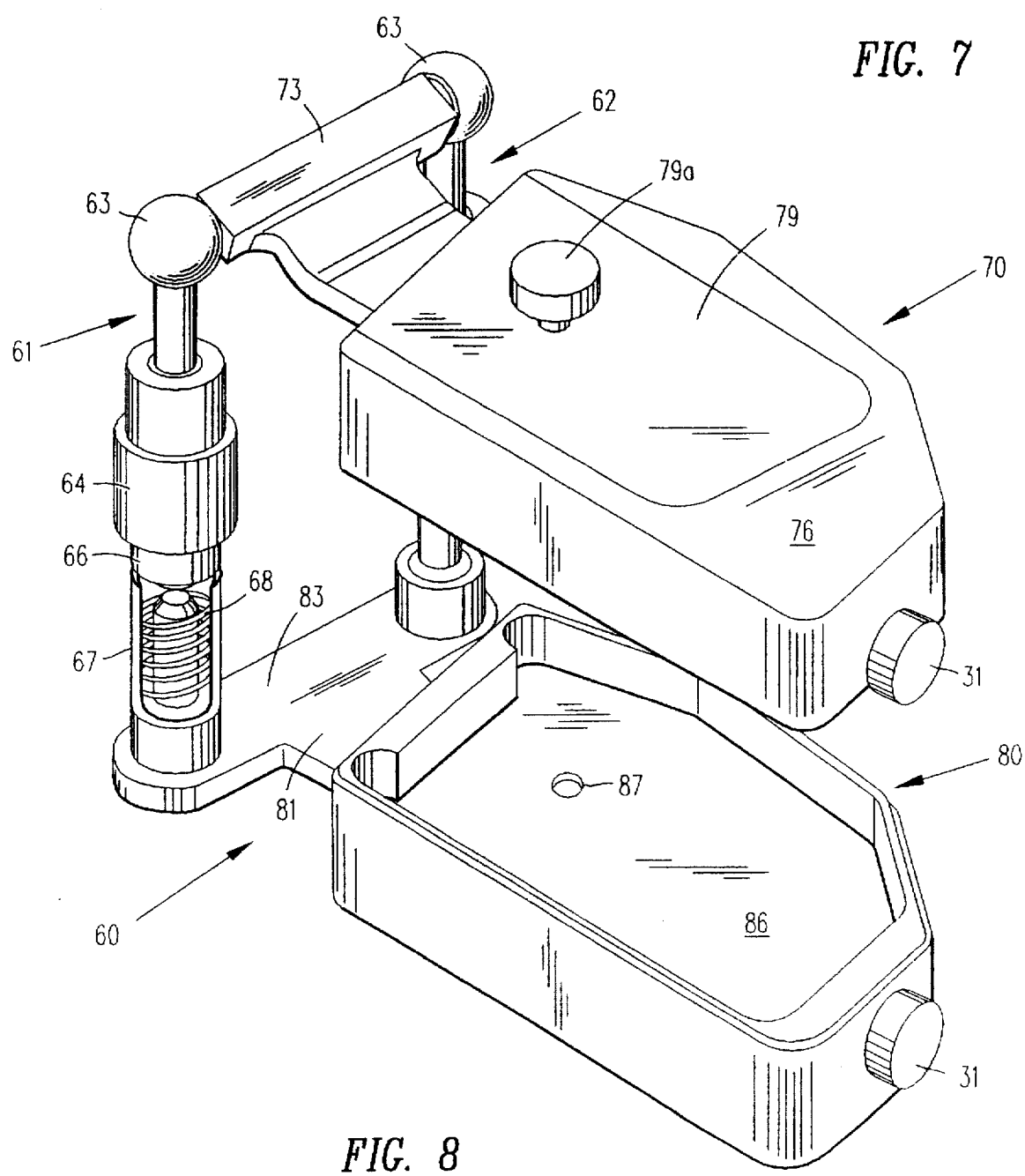
FIG. 8 is a perspective view of a half quadrant simplified articulator adapted to incorporate a hard mold member mounting a dental model.
Figure 9:
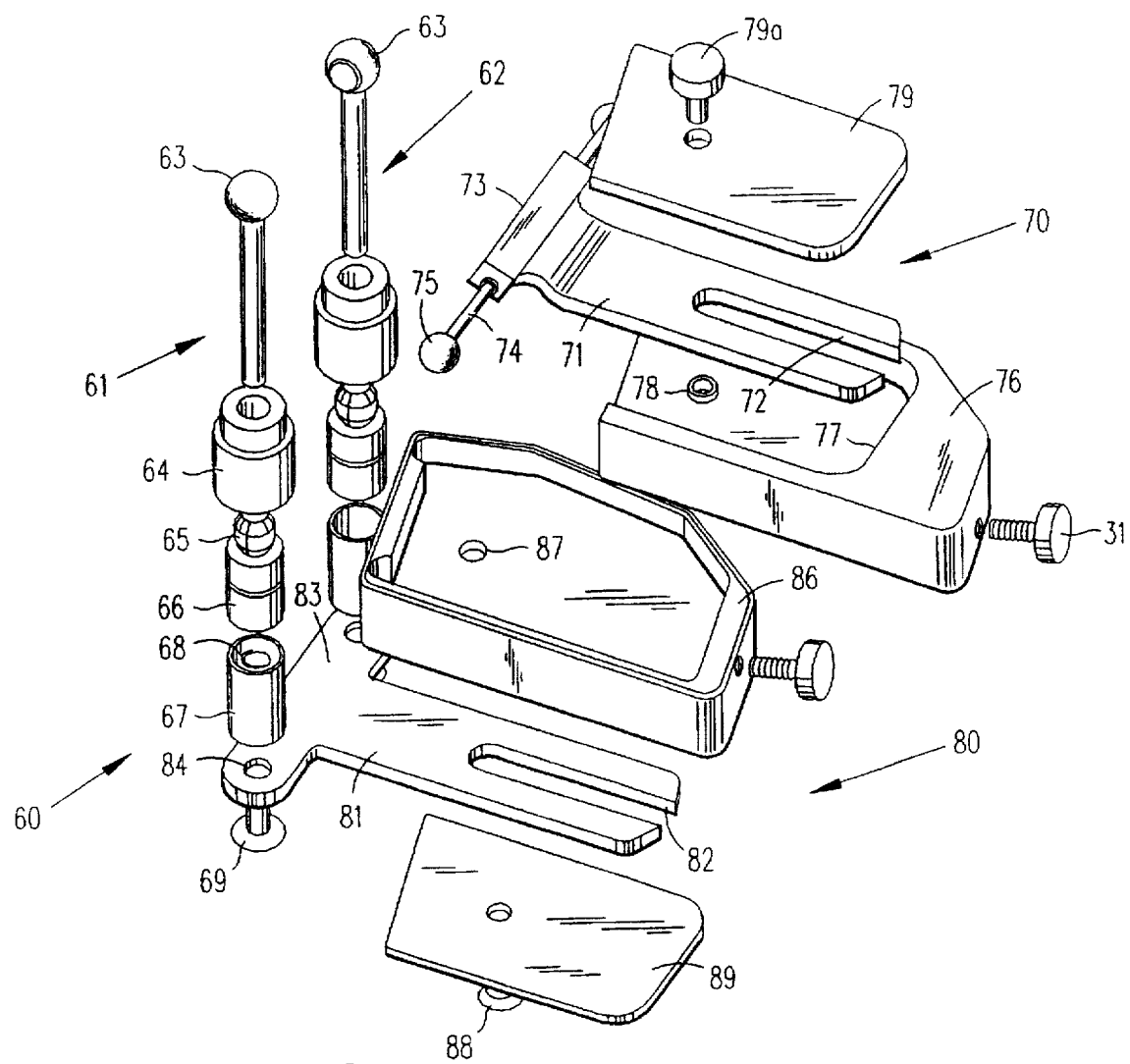
FIG. 9 is an exploded view thereof.

FIGS. 8 and 9 illustrate a half-quadrant articulator 60 including adjustable spring supports 61 and 62 providing a pivoted articulator top 70 and a fixed articulator base 80. Each of the spring supports includes a rod end ball shell 63, a screw vise 64, a collet 65, a pin vise 66, a support shell 67, a compression spiral spring 68 attached between the collet and shell, and a securing screw 69.

The articulator top 70 includes a T-fork 71 with a slot 72 at a distal end with a square ball holding rod 73 supporting a ball shaft 74 and having a 0.63 cm ball 75 at each end. The respective balls are press-fitted into the ball shells 63. An inverted quadrant tray 76, having a longitudinal open-ended slot 77 and a circular fixed boss 78 is slidingly fitted on the T-fork with the boss 78 in T-fork slot 72. A top cover 79 is positioned over the T-fork and tray slot 77 and attached thereto by a thumb screw 79a screwed into a threaded interior of boss 78. Upon loosening screw 79a, the tray 76 and its cover 79 may be slid to a desired longitudinal position with respect to the T-fork 71 and clamped at that location by turning screw 79a. The interior of the tray 76 is similar to the trays 24 and 26 differing only in that it is dimensioned and configured to accommodate only a one-half quadrant of a hard mold member. A securing thumb screw 31 as seen in FIG. 1 may be used to hold the hard mold member quadrant in the configuration matching confines of the tray interior as in FIGS. 3–5.

The articulator base 80 includes a second T-fork 81 with a distal end slot 82 and a top crosspiece 83 having a threaded bore 84 for reception of support screw 69. As in the articulator top 70, a bottom cover plate 89 which acts as a substage or subplate (as does cover plate 79) is secured to a bottom tray 86, including a slot therein for reception of the T-fork, by a thumb screw 88 extending from the underside of cover plate 89 through slot 82 into a threaded bore 87 in the bottom of tray 86 or extending partially into the tray bottom. Tray 86 and cover plate 89, upon loosening screw 88 is longitudinal positionable at any location along T-fork slot 82 and fixed thereat by tightening screw 88 into the tray bottom. The articulator top is pivotable about the support ball shells and may be articulated at various angular orientations by the spring flexibility of supports 61 and 62.

Figure 10:
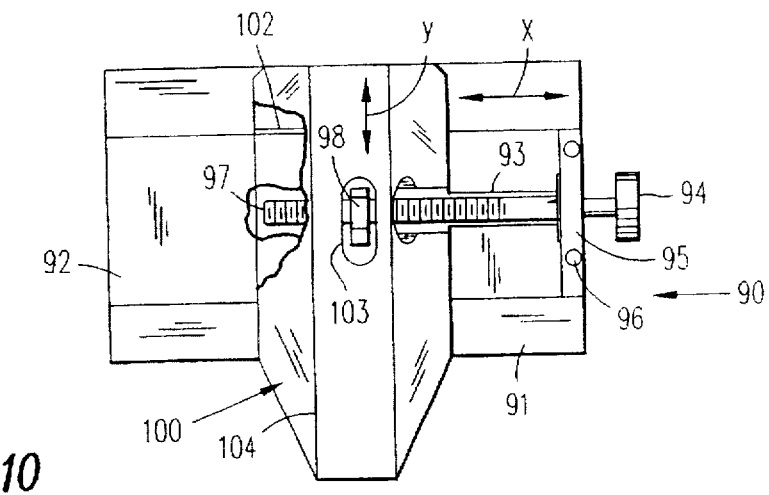
FIG. 10 is a top view of a preferred X and Y axis slide usable with the articulator of FIGS. 1–7.

FIG. 10 illustrates a preferred stage slide mechanism for the tray 26 supported on the articulator base and substage 25. It allows for both the longitudinal Y-axis movement as shown in FIGS. 1 and 2 and for lateral excursion of the substage 25 and bottom tray 26. Heretofore, lateral movement in articulators has been provided by the joint flexibility in the mechanical connections of the pivoted articulator top. Having a lateral adjustment on the articulator base and in the lower tray more approximates the natural lower jaw movement of a human. Thus, a dental technician can position a patient's lower arch and dental model to be more representative of its normal position and position the patient arch relative thereto with more accuracy. A two-stage slide 90 includes a stage base 91 which is a modified substage having a transverse X-axis dovetail tongue 92 machined on its top surface. One end of the tongue 92 includes a milled slot 93 for reception of threaded thumb screw 94 journalled in a bearing block 95 held by screws 96, and a milled slot 97 for receiving the end of screw 94 and for capturing a drive nut 98 threaded on screw 94. A top slide 100 includes a transverse dovetail groove 102 which coacts with dovetail tongue 92 to provide interconnected sliding movement therebetween. The top slide includes a medial slot 103, the edges of which abuts drive nut 98 such that as thumb screw 94 is turned clockwise the upper stage 100 moves to the right to any position until it abuts bearing block 95. Counterclockwise turning of screw 94 moves stage 100 to the left to any position along dovetail tongue 92 to a maximum amount dictated by the length of the screw 94 and slot 97. The top of stage 100 includes a longitudinal dovetail tongue 104 which fits into the groove 35 (FIG. 2) of a tray 26 positioned on top of stage 100. The clamping block screws 96 also attach the first stage 91 to an articulator base 11 (FIG. 1). The double headed arrows indicate the X-axis transverse movement of stage 100 with respect to stage 91 and the Y-axis longitudinal movement of the tray (not shown) with respect to stage 100, the latter along tongue 104.

The above description of embodiments of this invention is intended to be illustrative and not limiting. Other embodiments of this invention will be obvious to those skilled in the art in view of the above disclosure.

I claim:

1. The combination of a plasterless articulator and first and second hard mold members each member mounting a dental model, said articulator comprising:

a generally flat fixed base and a pivoted top;

a first tray mounted on said base, said first tray including upstanding fixed first side wall elements dimensioned and spaced for reception of the first hard mold member, said first hard mold member having a generally flat surface mounting a dental model including a positive cast of one of a patient's arches, at least multiple peripheral edge portions of the first hard mold member being dimensioned to abut and to conform to juxtaposed ones of said first side wall elements; and a second tray depending from said pivoted top and facing said first tray, said second tray including depending fixed second side wall elements dimensioned and spaced for reception of the second hard mold member, said second hard mold member having a generally flat surface mounting a dental model including a positive cast of a second of a patient's arches, at least multiple peripheral edge portions of the second hard mold member being dimensioned to abut and conform to juxtaposed ones of said second side wall elements; and wherein said hard mold members are mounted within the respective trays in a snap press fit.

2. The combination of claim 1 wherein each of said first and second side wall elements comprise a continuous wall corresponding in an inner peripheral shape to an overall outer peripheral edge shape of the first and second hard mold members.

3. The combination of claim 1 wherein said first and second side wall elements each comprise a series of spaced posts extending from each tray, said posts being spaced to abut the multiple peripheral edge portions of the hard mold members.

4. The combination of claim 1 wherein said first and second side wall elements comprise a continuous wall having a series of straight segments approximating a peripheral shape of the hard mold members, and wherein multiple ones of the peripheral edge portions of the hard mold members are spaced to tangentially abut a portion of said straight segments.

5. The combination of claim 1 further comprising a linear tongue extending from said base; and wherein said first tray includes a linear bottom groove in sliding connection with said tongue for adjusting said first tray along a longitudinal axis of said base.

6. The combination of claim 5 further including a locking screw extending through said base for locking said tray to a desired position on the longitudinal axis of said base.

7. The combination of claim 1 further comprising a universally mounted fixed slider member on said pivoted top, said slider member having a depending linear tongue; and wherein said second tray includes a linear groove in sliding connection to said depending linear tongue for adjusting said second tray along a longitudinal axis of said slider member.

8. The combination of claim 1 wherein a rear peripheral surface of the hard mold members extends transversely and straight across a root of the positive casts and rear ones of said side wall elements extend transversely and straight across a longitudinal axis of said trays.

9. The combination of claim 8 further comprising at least two clamping screws extending through portions of said side wall elements opposite said rear ones of said side wall elements, said clamping screws having flat ends not piercing the hard mold members.

10. The combination of claim 1 in which each of the hard mold members mount a positive cast of a full arch of a patient.

11. The combination of claim 1 in which each of the hard mold members mount a positive cast of a half arch of a patient.

12. The combination of claim 1 wherein a distal end of said fixed base extends under said first tray, said fixed base having a longitudinal slot; and wherein a first clamping plate and clamping pin on an underside of said base, clamps said first tray to said fixed base.

13. The combination of claim 1 wherein said pivoted top includes a slotted distal end overlying said second tray and a second clamping plate and clamping pin clamping said second tray to said pivoted top.

14. The combination of claim 1 including linear longitudinal slides between said base and said first tray and between said top and said second tray each of said trays being lockable at various positions with respect to said base and said top, respectively.

15. The combination of claim 14 further comprising a transverse slide between said base and said first tray.

16. The combination of claim 15 where said longitudinal slides and said transverse slide are dovetail tongue and groove slides.

17. The combination of claim 14 wherein the longitudinal slide between said base and said first tray further comprises a two-stage slide including a slide transverse to said longitudinal slide for lateral movement of said first tray with respect to said base.

18. An articulator having a generally flat fixed base and a pivoted top;

a first tray mounted on said base, said first tray including upstanding first side wall elements dimensioned and spaced for reception of a first hard mold member having a generally flat surface mounting a positive cast of one of a patient's arches, at least multiple peripheral edge portions of the first hard mold member being dimensioned to abut juxtaposed ones of said first side wall elements; and a second tray depending from said pivoted top and facing said first tray, said second tray including depending second side wall elements dimensioned and spaced for reception of a second hard mold member having a generally flat surface mounting a positive cast of a second of a patient's arches, at least multiple peripheral edge portions of the second hard mold member being dimensioned to abut juxtaposed ones of said second side wall elements;

linear longitudinal slides between said base and said first tray and between said top and said second tray;

further comprising a transverse slide between said base and said first tray; and wherein said transverse slide includes a captured drive nut to drive a first stage transversely of a longitudinal axis of said first tray.

19. A dental articulator comprising a first tray and a second tray each adapted to receive a first hard mold member mounting a first dental model and a second hard mold member mounting a second dental model;

said first tray including upstanding fixed side wall elements on a first surface dimensioned to receive the first hard mold member and a linear bottom groove on an opposite second surface;

a fixed first tray base including a first linear tongue having a first linear slot, said first tray being movable linearly with respect to said first linear tongue, and means for clamping said first tray at a desired longitudinal position with respect to said first linear tongue;

a second tray including depending fixed side wall elements on a first surface dimensioned to receive the second hard mold member, and a linear top groove on an opposite second surface;

a slider member including a second linear tongue having a second linear slot, said second tray being movable linearly with respect to said second linear tongue, and means for clamping said second tray at a desired longitudinal position with respect to said second linear tongue; and a pair of spring supports interconnecting said first tray base and said slider member, said slider member being universally mounted to said spring supports such that said slider member, said second tray and a mounted second hard mold member are together pivotable with respect to said fixed first tray base.

20. The articulator of claim 19 in which each of said spring supports include a ball shell and said slider member includes a pair of spaced balls in press-fitted interconnection with respective ones of said ball shells.

* * * * *